(12) United States Patent
Fischer et al.

(10) Patent No.: US 7,550,259 B2
(45) Date of Patent: Jun. 23, 2009

(54) LINEAR HIGH-THROUGHPUT PROTEOMICS

(75) Inventors: Steven M. Fischer, Hayward, CA (US); Christine A. Miller, Campbell, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 38 days.

(21) Appl. No.: 11/484,912

(22) Filed: Jul. 12, 2006

(65) Prior Publication Data
US 2008/0014603 A1    Jan. 17, 2008

(51) Int. Cl.
*C12Q 1/00* (2006.01)
(52) U.S. Cl. .......................................................... 435/4
(58) Field of Classification Search ....................... None
See application file for complete search history.

(56) References Cited

OTHER PUBLICATIONS

Walcher et al. "Characterization of a variant of the spinach PSII type I light-heavesting protein using kinetically controlled digestion and RP-HPLC-ESI-MS", Anal. Chem. 2003, 75:6775-6780.*
Mortz et al. "Mass spectrometric characterization of glycosylated interferon-gamma variants separated by gel electrophoresis", 1996, 17:925-931.*
Steen et al., "The ABC's (and XYZ's) of Peptide Sequencing", Nature Reviews vol. 5, pp. 699-711 (2004).

* cited by examiner

*Primary Examiner*—Jon P Weber
*Assistant Examiner*—Bin Shen

(57) ABSTRACT

A method of analyzing a sample comprising multiple protein species is provided. The proteins are separated by species such that the multiple protein species emerge in a sequential order and are then digested in the sequential order in which they emerge from the separation process. The digested proteins are introduced into a mass spectrometer in the same sequential order so that, within a given time window, the digested proteins introduced into the mass spectrometer are covariant.

24 Claims, 8 Drawing Sheets

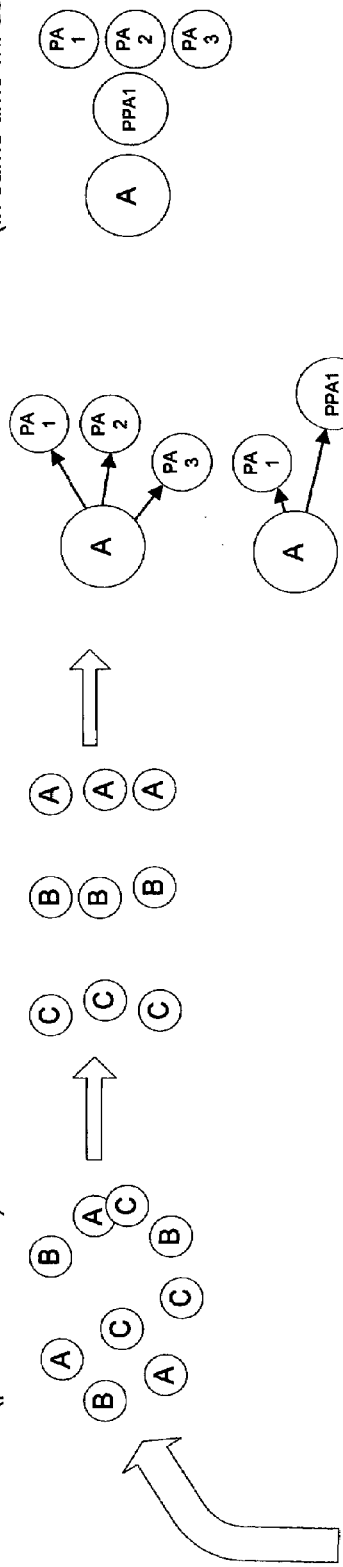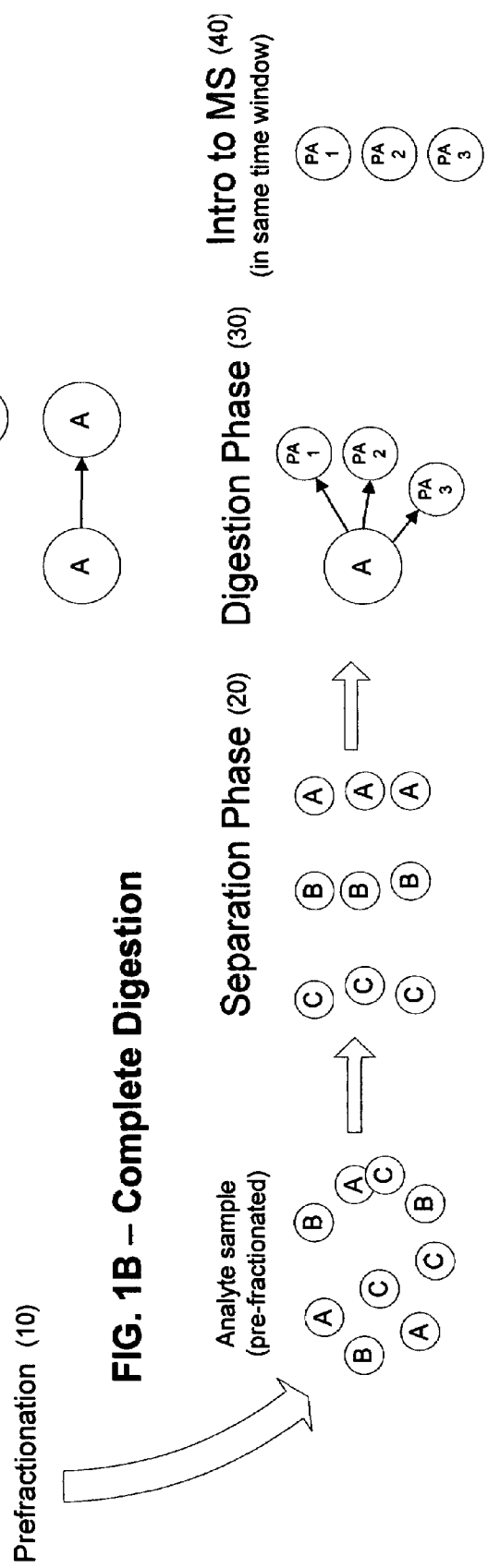
FIG. 1A – Incomplete Digestion
FIG. 1B – Complete Digestion

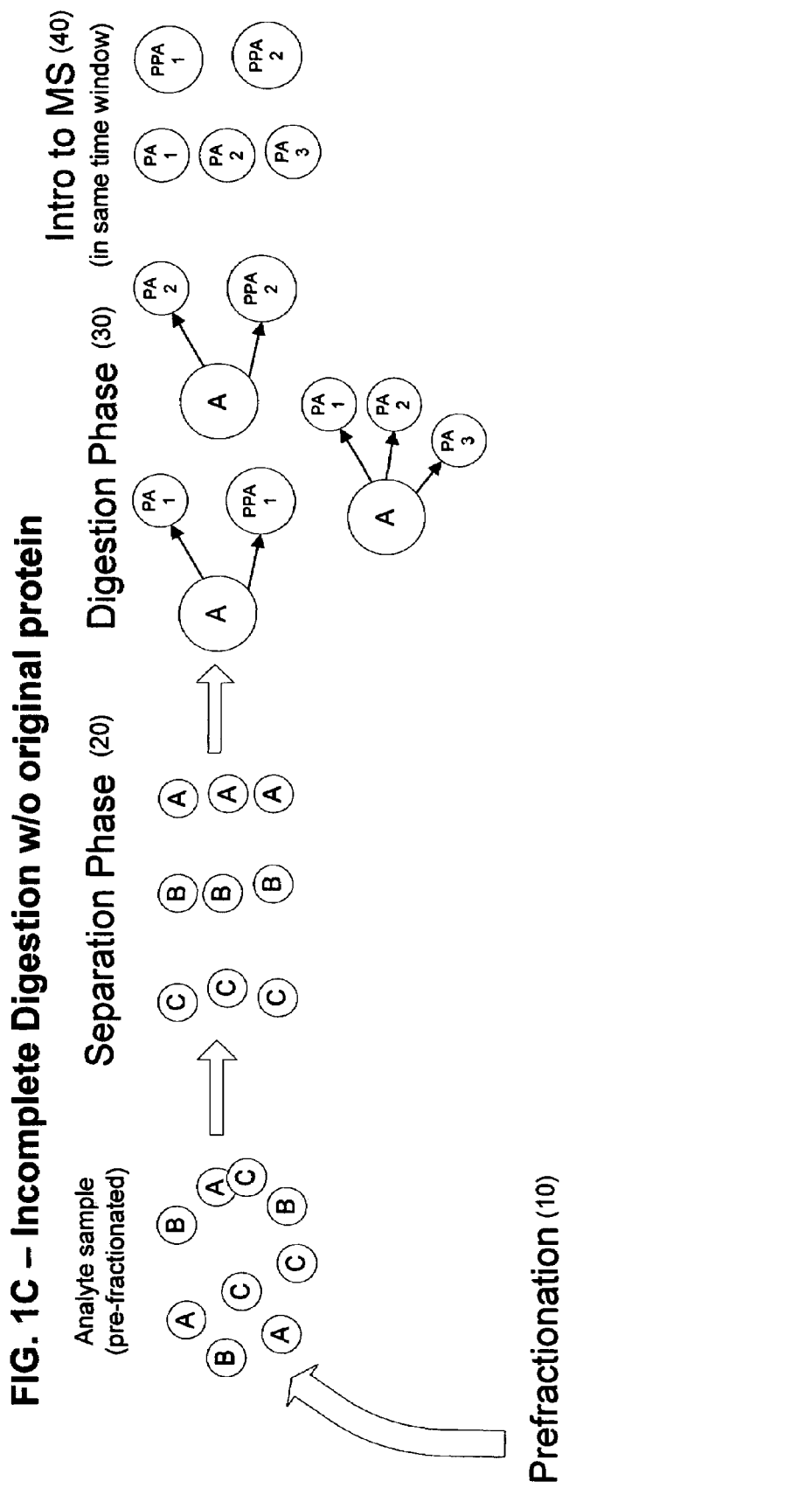

Series of mass spectra taken within time window t
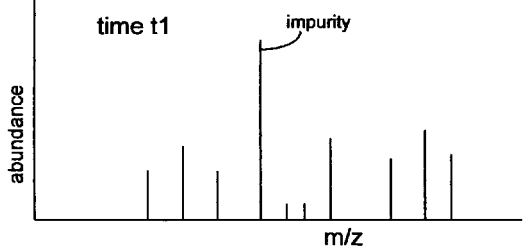
FIG. 5A time t1
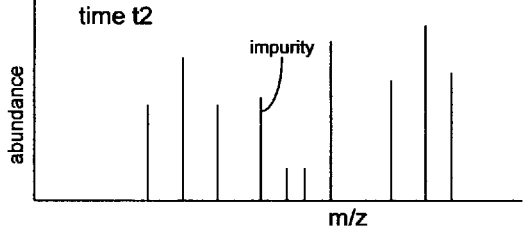
FIG. 5B time t2
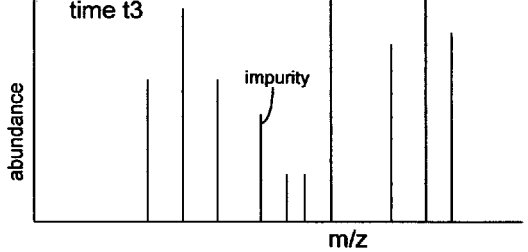
FIG. 5C time t3
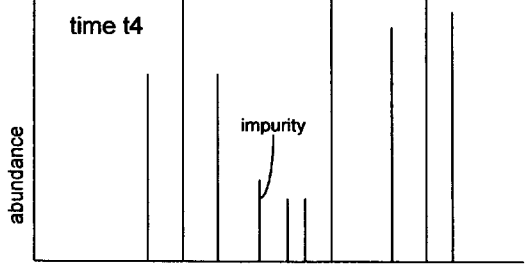
FIG. 5D time t4
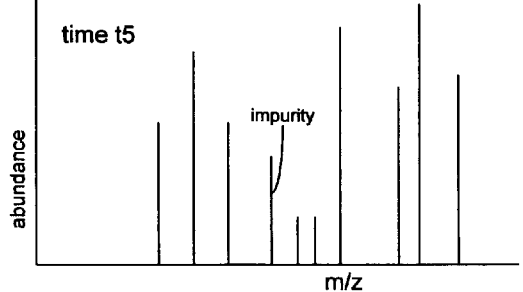
FIG. 5E time t5
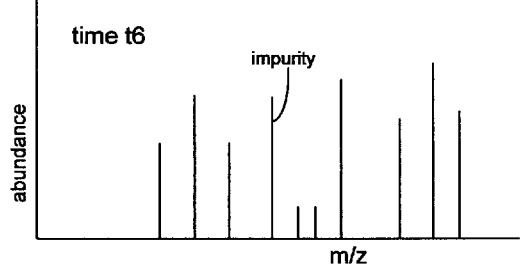
FIG. 5F time t6
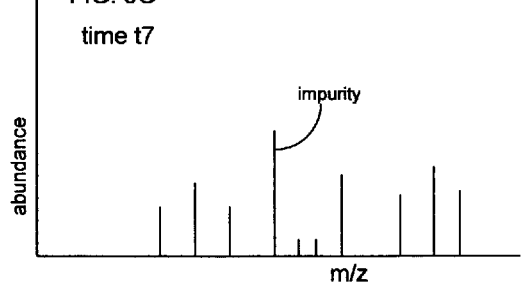
FIG. 5G time t7

LINEAR HIGH-THROUGHPUT PROTEOMICS

BACKGROUND INFORMATION

Mass spectrometry has proven to be useful for identifying and elucidating the structure of complex molecules, and is particularly important in the study of proteins. In particular, the field of proteomics relies to a large extent on various mass spectrometry techniques to examine proteomes, the total set of proteins generated within a particular cell as derived from its genome, and partial proteomes, such as the set of proteins within a specific organelle within a cell.

There is an obvious limitation in applying mass spectrometric techniques in this area, however, in that it is impossible to determine the identity of a large protein molecule solely on the basis of its mass-to-charge ratio taken from a mass spectrum of the protein, and further information is required for identification and to determine molecular structure. To provide supplemental information, large proteins may be broken into smaller constituent peptides by enzymatic digestion prior to mass analysis and/or may be fragmented within a mass spectrometer by collision-induced dissociation (CID) or by electron capture dissociation (ECD); when the digest (the peptides produced by a digestion) or the fragment ions (the constituents produced by physical fragmentation) derived from a single protein are analyzed in a mass spectrometer, the resulting spectrum may provide a peptide mass fingerprint and/or peptide sequence information through which a protein may be identified and characterized.

As noted above, in typical proteomics applications sample proteomes or partial proteomes contain multiple proteins. But when a mixed sample is digested and analyzed without prior separation, the resulting analysis is complicated, since there is no way to tell which peptides are associated with each other as constituents of a specific protein. Thus, high protein sequence coverage is not usually achieved from a digest of a mixed protein sample. This problem can occur even in cases where conventional steps are taken to separate proteins. For example, when gel electrophoresis is performed to separate proteins spatially, the individual protein spots are not always completely distinct and multiple proteins may be included in a removed spot.

Moreover, in applications in which the aim is to analyze different proteins simultaneously, a mixed protein sample is required, with the result that the chromatogram will contain numerous peaks and the mass spectrum will necessarily contain numerous ions representing peptides derived from a number of different proteins, leading to the aforementioned difficulties in identification and characterization.

SUMMARY OF THE INVENTION

To address this problem, the present invention provides a linear throughput process for preserving the association of digested and/or fragmented proteins during mass spectrometric analysis, so that identification and structural elucidation is facilitated.

In one aspect, the present invention provides a method of analyzing a sample comprising multiple protein species in which proteins are separated by physio-chemical processes such that the multiple protein species emerge in a sequential order with some degree of physical separation and are then digested in the sequential order in which they emerge from the separation process. The digested proteins are introduced into a mass spectrometer in the same sequential order so that, within a given time window, the peptides from a digested protein are introduced into the mass spectrometer and are covariant. This method provides an on-line linear throughput method that can be employed continuously over a long duration.

In different embodiments of the method of analyzing a sample comprising multiple proteins according to the present invention, the digesting phase can be performed: incompletely such that a portion of the separated proteins are not digested and are introduced in their original form into the mass spectrometer with their corresponding covariant digestion-produced peptides; or extensively such that none of the separated proteins are introduced intact into the mass spectrometer and substantially all of the separated proteins are broken down into peptides.

In another aspect, the present invention provides a method of preparing a sample comprising multiple protein species for use in matrix-assisted laser desorption ionization (MALDI). In an embodiment of this method, the proteins are separated by physio-chemical properties such that the multiple protein species emerge in a sequential order and are then digested in the sequential order in which they emerge from the separation. In another embodiment, at regular time intervals, the covariant digested peptides emerging from the separation and subsequent protein digestion is then deposited onto a spot of a MALDI support plate. The mass spectral analysis is performed offline but makes use of the sequential protein separation and the known ionization benefits of the MALDI technique. This technique may be particularly applicable for detailed protein characterization.

In a further aspect, a microfluidic device for receiving a multiple protein sample and for providing covariant peptides to a mass spectrometer is provided. The microfluidic device includes a separation chamber including means for separating the multiple proteins in the sample by physio-chemical properties such that the multiple protein species emerge in a sequential order and a digestion chamber coupled to the separation channel including enzymes for digesting the separated proteins in the sequential order in which they are received from the separation channel. The digestion chamber is coupled via an outlet to an interface through which digested peptides are delivered to the mass spectrometer.

BRIEF DESCRIPTION OF THE DRAWINGS

FIG. 1A shows an embodiment of the linear throughput method according to the present invention in which protein digestion is performed incompletely and a portion of the original protein survives digestion intact.

FIG. 1B shows another embodiment of the linear throughput method according to the present invention in which protein digestion is performed to completion.

FIG. 1C shows another embodiment of the linear throughput method according to the present invention in which protein digestion is performed incompletely but none of original protein survives digestion intact.

FIGS. 5A-5G show a series of mass spectra taken during time window t shown in FIG. 4

DETAILED DESCRIPTION

Figure 2A:
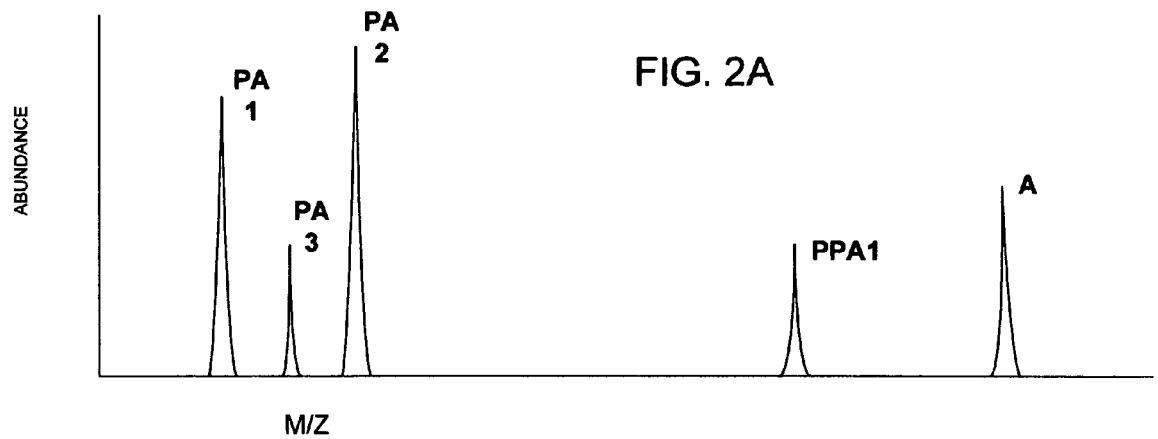
FIG. 2A shows an example mass spectrum of the products of an incomplete digestion process where a portion of the original protein remains intact, corresponding to the linear throughput method shown in FIG. 1A.

As used in this specification and the appended claims, the singular forms "a," "an," and "the" include plural referents unless the context clearly dictates otherwise.

According to the present invention, a linear throughput method for analyzing proteins is provided to address the problem of the lack of association of peptides to each other and to particular proteins during spectrometric analysis, so that they may be more accurately identified and characterized. In this linear throughput method, the relationship between peptides (or digested proteins, which may include polypeptides when digestion is incomplete) that are constituents of the same protein is maintained. The term used herein to describe this relationship among the peptides derived from a single protein is "covariant". Each set of covariant digested proteins is analyzed within the same time window within a mass spectrometer and inversely, digested proteins that are not covariant are not analyzed within the same time window.

FIGS. 1A, 1B and 1C schematically illustrate three example embodiments of the linear throughput method of the present invention. The embodiments differ with respect to the level of digestion to which separated proteins are subjected, as will be explained in greater detail below.

Generally speaking, protein samples used in proteomic studies can include thousands of different proteins. To reduce the number of protein species to a more manageable number for high-throughput analysis, the protein samples are pre-fractionated (10) to yield smaller sub-sets of protein molecules. There are a number of different techniques known to those of skill in the art available for implementing the pre-fractionation process (10) including two-dimensional polyacrylimide gel electrophoresis (2D-PAGE), liquid-phase separation methods such as high performance liquid chromatography (HPLC) or capillary electrophoresis, and affinity-binding methods.

It is intended for the pre-fractionation process (10) to yield fractions containing a much smaller set of proteins, for example, between 3 and 20 distinct species, more amenable for the following throughput steps and subsequent analysis. In the example embodiment shown in FIG. 1A, the pre-fractionation process yields a group of three proteins A, B and C, which is referred to herein as the analyte sample. The analyte sample, which represents a selected fraction derived from the pre-fractionation process (10), then undergoes a second separation phase (20). The separation phase (20) may be implemented online by liquid chromatography in micro or nano scale channels (or chambers) of a microfluidic chip device, for example. Affinity binding may also be used in this context. In general, microfluidic separation techniques that may be used in the context of the present invention are well known in the art. For example, commonly assigned U.S. Pat. No. 6,958,119 to Yin et al. entitled "Mobile Phase Gradient Generation Microfluidic Device" describes a microfluidic device that may be used in the implementation of the separation phase (20).

It is beneficial to use a different 'orthogonal' technique in the separation phase (20) from the technique used in the pre-fractionation process (10), which relies on different physical parameters. For example, if the pre-fractionation process (10) is implemented using gel electrophoresis which separates protein according to pI and molecular weight, then the separation process (20) may be implemented using reverse phase liquid chromatography that separates according to relative hydrophobicity. Using orthogonal, or multidimensional, separation techniques can significantly increase the resolving power of the separation process as a whole and also reduces biases associated with any single particular separation technique.

One of the significant features of the separation process (20) applied to the analyte sample, is that it separates the species A, B and C differentially, such that the species are output from the process in a sequential order. In the example shown in FIG. 1A (and also in the other illustrated embodiments), protein A travels through the separation in the shortest time, followed by protein B and then protein C. It is desired that the sample complexity be small enough and the resolving power of the separation technique great enough such that each species emerge distinctly as illustrated without mixing of the species. However, complete separation is not required for this linear proteomic analysis to work, as long as there is some degree of spatial and temporal separation that enables groups of covariant peptides to be established (as shown, for example, in FIG. 4A, discussed below).

After the proteins are separated in phase (20), they are broken into constituent peptides in a digestion phase (30). The digestion phase (30) may be implemented by exposing the separated proteins to an enzyme such as trypsin as they are sequentially output from the separation phase (20). Other enzymes such as Lys-C or Asp-N and additional chemical techniques may also be used in this context depending on the protein species involved. The enzymatic digestive action on the proteins is generally rapid such that the sequential order of the throughput is not affected by the digestion, e.g., protein B does not enter the digestion phase and mix with protein A while protein A is being digested. The rapid reaction kinetics of the enzymatic digestion allows the digestion to take place extremely quickly on the order of the liquid flow rate.

The concentration of the enzyme can be varied using techniques well known in the art to control the level or completeness of digestion to which the proteins are subjected. For example, the higher the ratio of enzyme to protein substrate, the greater the amount and speed of digestion and the higher the likelihood that most of the protein will be broken down into constituent peptides; high ratios can be obtained by immobilizing the enzymes on inert beads or similar surfaces in a digestion chamber whereby the level can be determined by the number of beads (and their total surface area). Enzyme immobilization also has the effect of reducing background noise generated by detection of the enzymes themselves or unwanted auto-digestion by-products.

In the exemplary embodiment shown in FIG. 1A, the concentration of digestive enzymes is low enough that the protein digestion is incomplete; this allows a measurable level of the original protein and/or large polypeptide constituents much larger than fully digested peptides (which are on average less than 20 amino acids long) to survive the digestion phase (30). As illustrated in the figure, at the digestion phase (30), a portion of separated protein A is completely digested and broken down into peptides PA1, PA2 and PA3, another portion of protein A is incompletely digested into peptide PA1 and a polypeptide molecule (PPA1), and a further portion of protein A is not digested at all and passes through the digestion phase intact. The complete end product of the digestion phase (30) in this case thus includes peptides PA1, PA2 and PA3, polypeptide PPA1 and protein A, which can then be introduced into a mass spectrometer for analysis by the techniques discussed in greater detail below.

One of the advantages of performing an incomplete digestion in this manner is that the original protein A is preserved with the co-variant peptides PA1, PA2 and PA3. FIG. 2A illustrates a mass spectrum obtained from analysis of the output from the incomplete digestion of protein A including A, PPA1, PA1, PA2, PA3. It is understood that this mass spectrum is merely illustrative and is not meant to represent the mass spectrum of any actual protein. When the peptides PA1, PA2, PA3 and protein A are analyzed in the same time window, the mass of protein A can be used as a limiter during a database search when determining the identity of protein A from the mass spectrum of the peptides PA1, PA2 and PA3 (peptide mass fingerprinting). The protein mass information can be used as a further constraint to facilitate characterization and analysis.

Figure 2B:
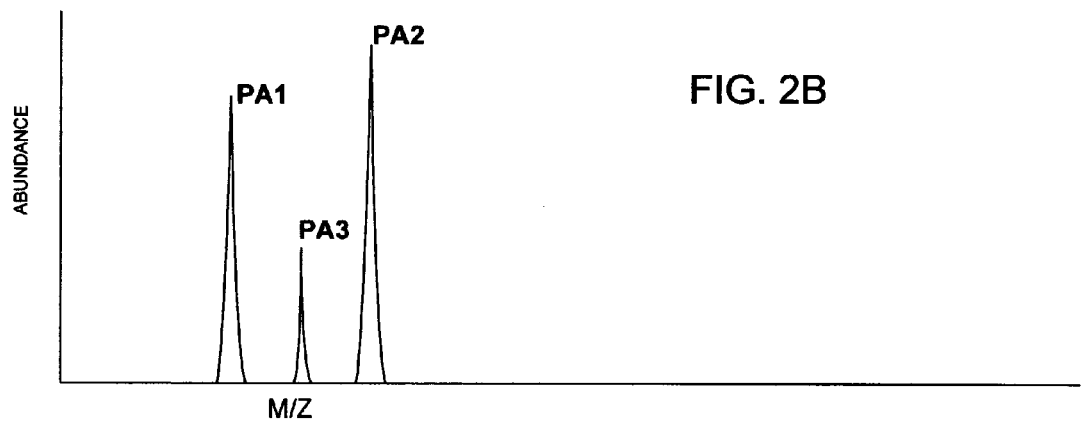
FIG. 2B shows an example mass spectrum of the products of a complete digestion process which corresponds to the linear throughput method shown in FIG. 1B.

In the embodiment of the linear throughput process of the present invention depicted in FIG. 1B, the concentration of the digestion enzymes is set higher in order to provide complete digestion of the proteins in the digestion phase (30). In this case, during the digestion phase (30) protein A is completely digested into peptides PA1, PA2 and PA3. The resulting mass spectrum after introduction to a mass spectrometer (40) is shown in FIG. 2B. While the mass spectrum of peptides PA1, PA2, PA3 can possibly be useful for identification or characterization, generally the covariant peptides are collisionally fragmented for MS/MS analysis in order to obtain amino acid sequence information for each of the peptides, in this case of PA1, PA2 and PA3.

Figure 2C:
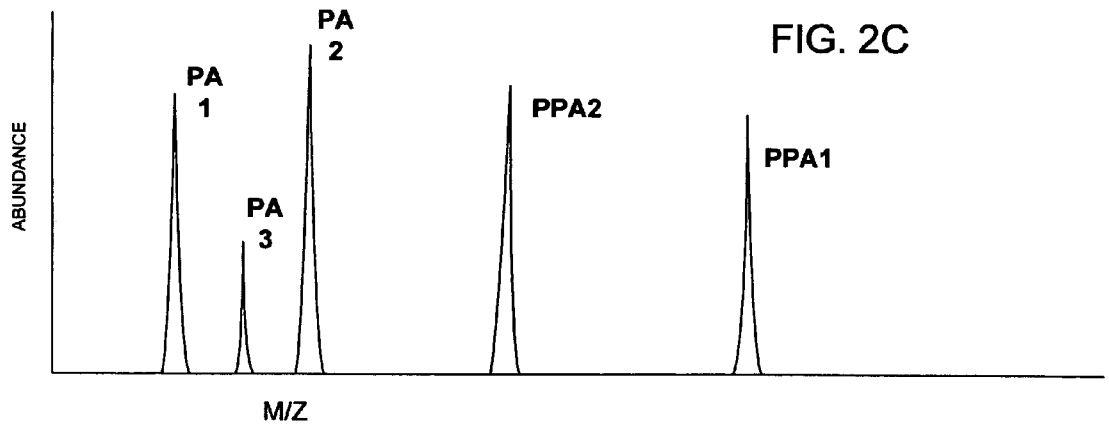
FIG. 2C shows an example mass spectrum of the products of an incomplete digestion process in which none of the original protein passes through intact, corresponding to the linear throughput method shown in FIG. 1C.

In the embodiment depicted in FIG. 1C, digestion is incomplete in that protein A is not completely broken down into small peptides, but yet none remains intact through the digestion phase (30). In this case, the products of the digestion phase (30) are peptides PA1, PA2, PA3 and polypeptides PPA1 and PPA2. A mass spectrum of the resulting products is shown is shown in FIG. 2C.

Figure 3A:
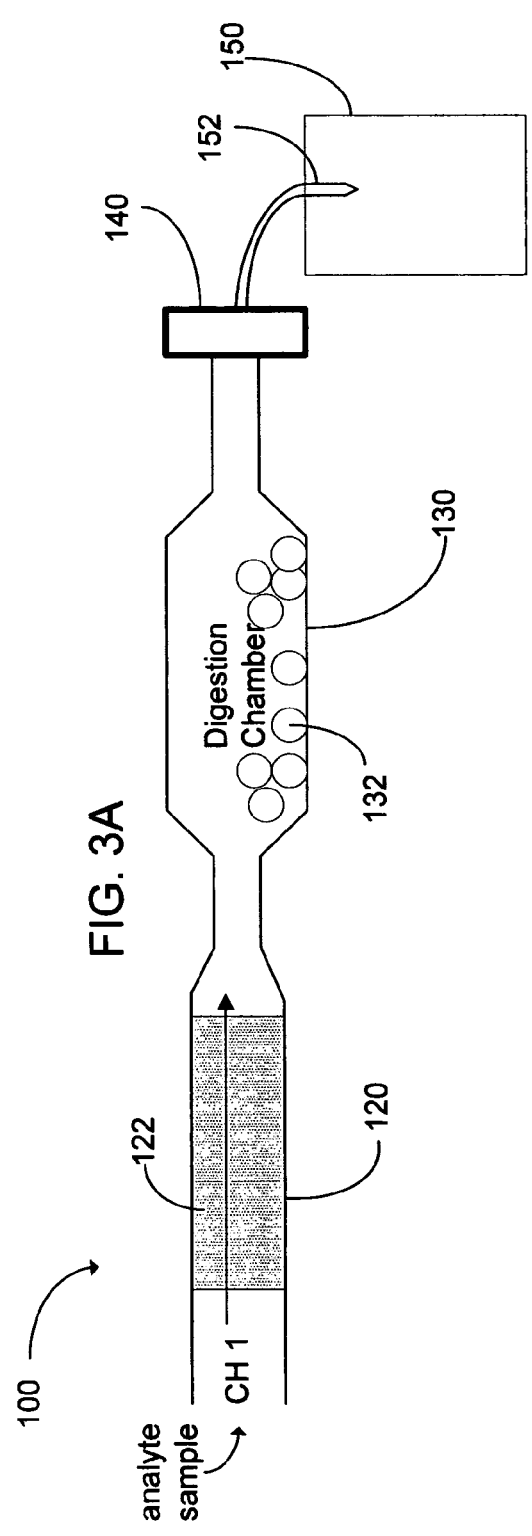
FIG. 3A shows an example section through a microfluidic device for separating and digesting proteins according to the present invention.

FIG. 3A shows an embodiment of an apparatus that can be used to implement the separation and digestion phases according to the present invention. The apparatus 100 can be implemented in a single-channel of a microfluidic device having several solution-filled chambers or reservoirs arranged in sequence. A pre-fractionated analyte sample including several proteins may be provided to the channel CH1 of the device 100 from an upstream position; the analyte sample then is moved downstream through the channel under fluid or osmotic pressure, for example.

As shown in FIG. 3A, a separation chamber 110 receives the analyte sample along channel CH1. The separation chamber 110 may include a separation medium 122 appropriate for the particular separation technique employed, e.g., chemically functionalized particles for affinity binding, a gel suitable for electrophoretic separation, etc. The proteins within the analyte sample traverse the separation chamber in a downstream direction and separate from each other within the medium 122 according to one or more physio-chemical properties so that there is some measurable and identifiable spatial separation of the proteins. It is again noted that the separation of the proteins need not be complete. For example, with reference to the example given above of proteins A, B and C, there may be corresponding time windows tw1, tw2 and tw3 in which a majority of the protein elutes out of the separation chamber. Continuing with the example, in time window tw1, 80% of protein A, 7% of protein B may elute from the separation chamber 120. However, in this example the amount of protein A that exits the separation chamber is, in relative terms, over an order of magnitude greater than the amount protein B that exits within the same time window, establishing a clear spatial and temporal separation between the predominant portions of proteins A and B.

Once separated partially or completely, the proteins flow downstream sequentially into a digestion chamber 130. The digestion chamber 130 includes an enzyme such as trypsin. The enzymes may be immobilized by being bonded to particles 132, which may comprise functionalized beads commonly used in the art to provide binding sites. The number and size of the beads 132 may be selected to produce a particular concentration of enzymes corresponding to the level of digestion desired. The concentration is sufficient to provide rapid reaction kinetics between the separated proteins and the enzymes so that digestion of the proteins occurs during the time period in which they traverse the digestion chamber 130.

Digested peptides and/or incompletely digested proteins elute from the digestion chamber and flow downstream to an interface device 140 that couples to the ion source 150 of a mass spectrometer. The interface device 140 may comprise a conduit such as a micro or nanocapillary that provides a specified volume of fluid per second to the inlet of the ion source 150. In one implementation, the ion source includes an electrospray element 152. The interface device 140 may be coupled directly to the electrospray element 152 allowing a continuous flow of samples through the microfluidic channel CH1 of apparatus 100 up to the electrospray element. The products of the digestion phase are in each case ionized in ion source 150, possibly fragmented within the mass spectrometer, detected, and then analyzed.

Figure 3B:
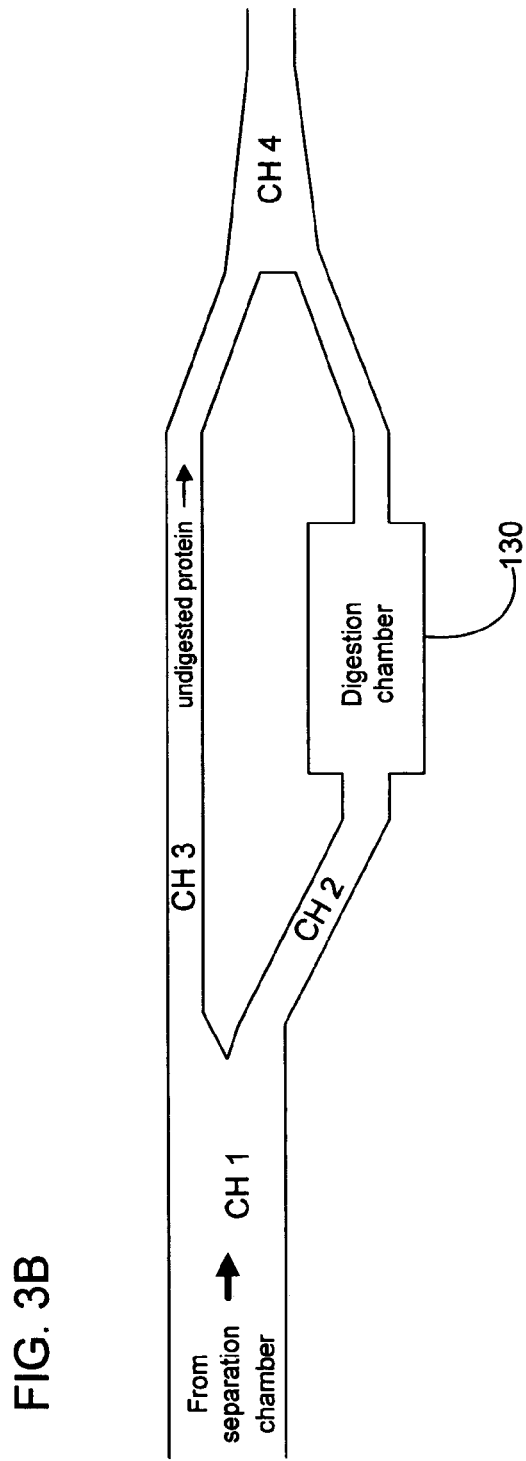
FIG. 3B shows an example section through a microfluidic device that may be used in the context of the present invention to combine an undigested protein with its covariant digested proteins.
Figure 3C:
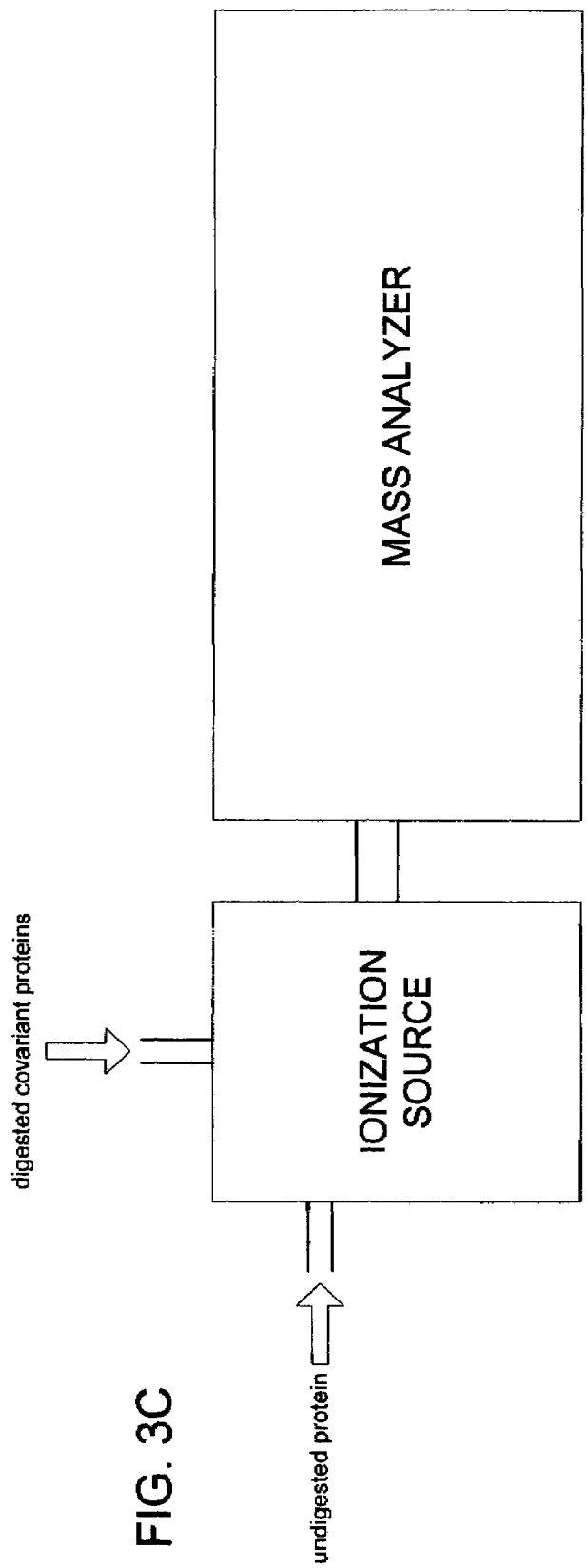
FIG. 3C illustrates a mass spectrometer having an ionization source with two inlets by which undigested protein can be multiplexed with its covariant digested proteins.

FIG. 3B shows another embodiment of an apparatus for separating and digesting a protein sample according to the present invention including an additional channel that diverts a portion of the separated proteins away from the digestion chamber along an independent path. This represents another mechanism (besides incomplete digestion) for preserving a portion of the original proteins intact for mass analysis. The aim is to maintain the covariant relationship between the protein and its constituent peptides, so that the mass information of the protein can be used in conjunction with its covariant peptide information. In FIG. 3B, proteins are sequentially eluted through a channel CH1 coming from a separation chamber (not shown). Downstream, channel CH1 splits into two channels CH2 and CH3. The proteins in CH2 pass through a digestion chamber, while the proteins in CH3 pass without being subject to digestion. Channels CH2 and CH3 recombine in channel CH4 which leads downstream to an interface device (also not shown) coupled to the ion source of a mass spectrometer. In another implementation shown schematically in FIG. 3C, the intact protein and its digestion products are not recombined in a flow channel but can be introduced via different inlet ports of a mass spectrometer ionization source, so that the intact protein is multiplexed with its covariant digested proteins during mass analysis.

Figure 4:
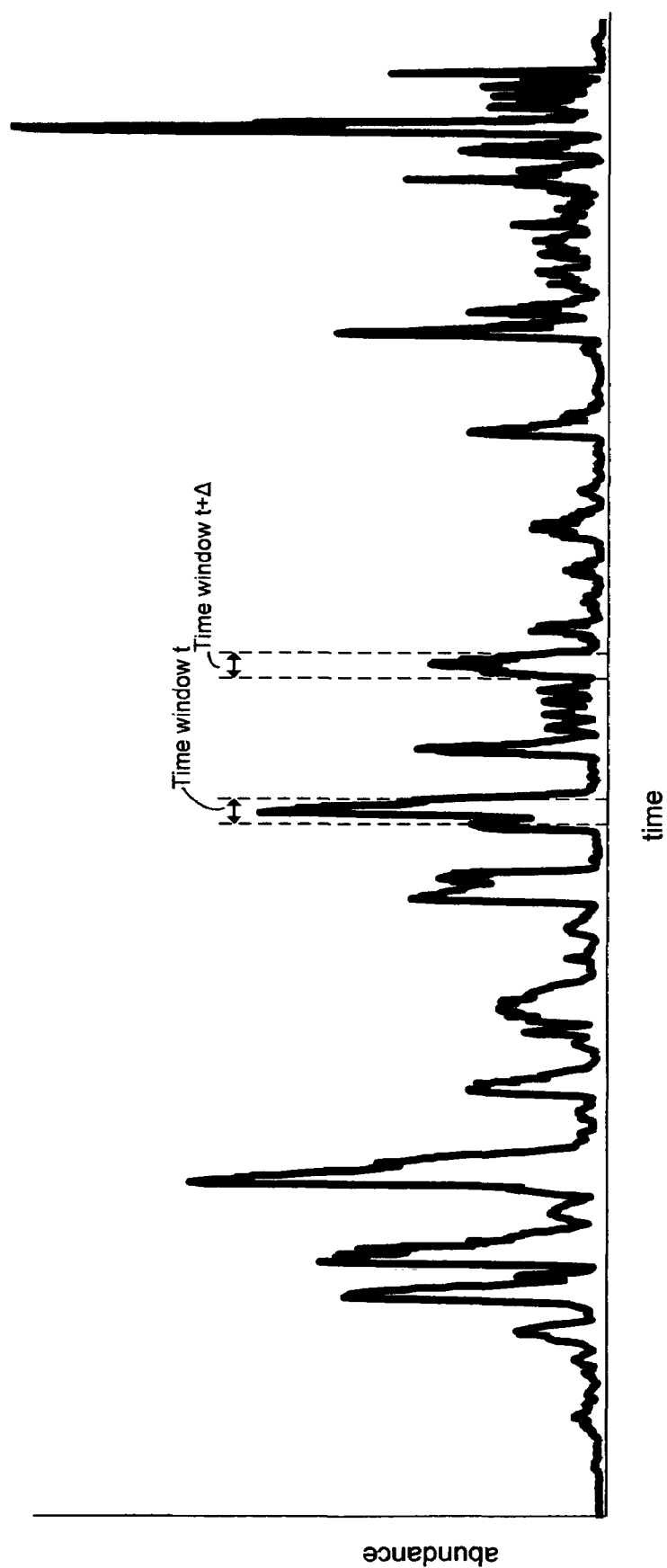
FIG. 4 is an example chromatogram of a protein sample separated and digested according to the present invention.

FIG. 4 is an example chromatogram of peptides separated and digested according to the present invention. The chromatogram indicates the abundance of peptides detected over time. One of the main benefits of the present invention is that the covariant relationship between peptides derived from the same protein is maintained within a given time window. In graphical terms, this means that a given time window of the chromatogram of FIG. 4, for example the time interval of an abundance peak identified as time window t, includes covariant peptides. FIGS. 5A through 5G show a series of mass spectra taken at small intervals in time window t, illustrating the covariance of most of the detected peptides and how such peptides can be identified when separation is not complete and 'impurities' (which in this case simply represent non-covariant peptides) are also detected within time window t.

FIGS. 5A to 5D are example mass spectra that illustrate the increasing abundance of covariant peptides as scans are taken from the front edge of the peak towards its center. As shown, FIG. 5B shows a doubling of the abundance shown in FIG. 5A, FIG. 5C shows a tripling, and FIG. 5D shows a quadrupling. Similarly, FIGS. 5E-5G show an analogous decline in abundance in scans taken after the top of the peak. Importantly however, it is noted that the ratio of all but one of peptide peaks do not change relative to one another during the series of spectra even as the overall abundance changes through the peak. In other words, the peptides that vary in the same ratio throughout the time series can be identified as covariant peptides, and those that do not can be identified as impurities. FIGS. 5A-5G show such an impurity that varies randomly without a defined relationship to the other peptides that rise and fall together.

As discussed above, proteins in some embodiments are introduced into the mass spectrometer at different times from their respective covariant digested proteins. For example, referring again to FIG. 3B, if the fluid travel durations through CH2 and CH3 are approximately equal, when split channels CH2 and CH3 recombine in channel CH4, the intact protein (of a given species) is combined with its digestion products. However, in general, the travel durations will not be the same, and at a given time, the intact protein entering channel CH4 from channel CH3 may not correspond to the digested products entering channel CH4 from channel CH2. Referring again to the chromatogram of FIG. 4, an intact protein (A) elutes after its covariant peptides (CovA) and is detected in the chromatogram during a different time window (t+Δ), where Δ represents the elution time difference, and its covariant peptides are detected in time window t (this is merely illustrative; in practice the intact protein is more likely to elute ahead of its covariant peptides).

To match the protein with its covariant peptides for identification purposes, an adjustment is required to account for the difference in arrival times between the intact protein and its corresponding covariant peptides. The difference between the average travel durations in the two channels CH2, CH3 can be measured experimentally. This difference (Δ) can be used to perform an adjustment (described in greater detail below) which can be implemented by a software algorithm executed by a processing unit that receives data from a mass spectrometer.

Figure 6A:
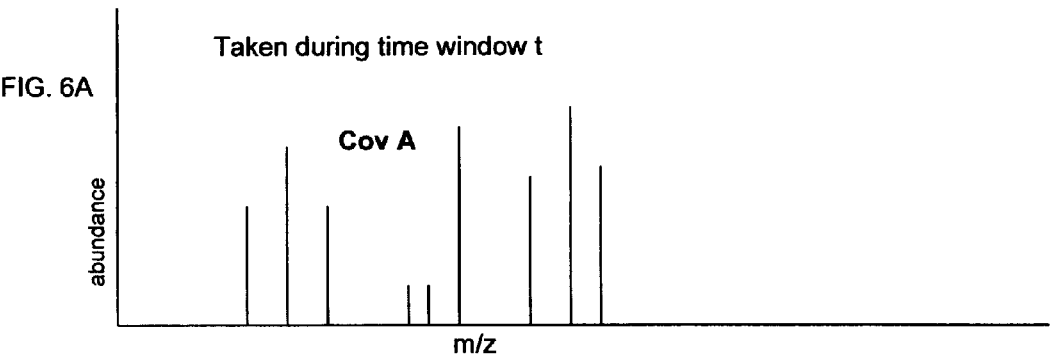
FIG. 6A shows an example mass spectrum of covariant peptides of protein A taken during time window t.
Figure 6B:
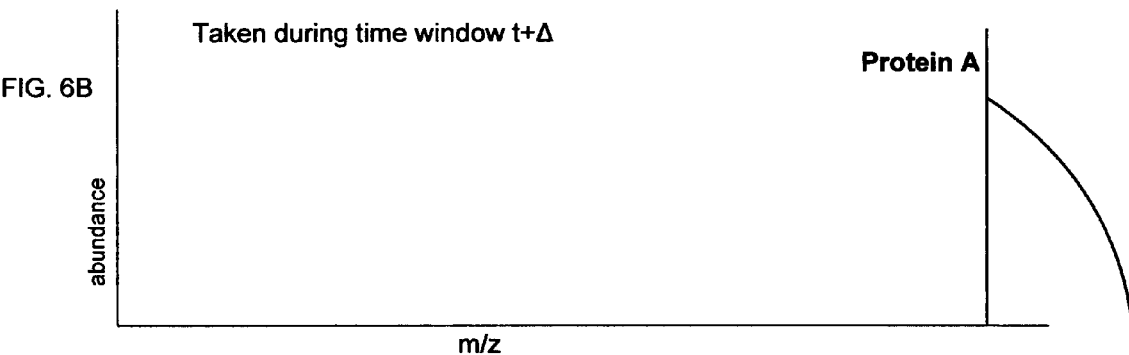
FIG. 6B shows an example mass spectrum including protein A taken during time window t+Δ.
Figure 6C:
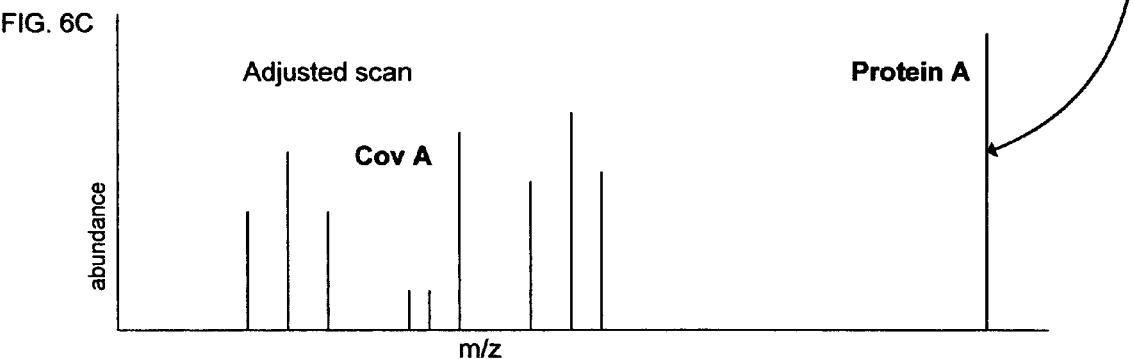
FIG. 6C graphically illustrates the method of associating protein A with its covariant peptides by compensating for the time difference in elution.

FIGS. 6A-6C are example mass spectra that graphically illustrate an adjustment made to associate an intact protein (A) with its covariant peptides (CovA). FIG. 6A shows the mass spectrum of CovA detected during time window t. FIG. 6B shows the mass/charge ratio of protein A detected during time window t+Δ; protein A is shown at the far right of the mass spectrum, indicating the comparatively high mass of the intact protein A. FIG. 6C graphically illustrates an embodiment of an adjustment method whereby the data collected on protein A in the mass spectrum of FIG. 6B is transferred to the mass spectrum of FIG. 6A. In this manner, the data of protein A is associated with its covariant proteins CovA which facilitates analysis of protein A and its covariant peptides.

This process may be accomplished in different ways. One example is by accounting for the time difference (Δ) between the elution times of protein A and covA. For example, let us say that it has been determined that intact proteins elute (Δ) seconds faster than it takes digested proteins to elute into the mass spectrometer. Software logic can be used to identify the intact protein A in mass spectra of FIG. 6B, for example by setting a m/z threshold beyond which a detected species can be considered to be a protein rather than a peptide. Once protein is identified, the elution time difference (Δ) can be added (or subtracted as the case may be) to shift data points of the proteins from their 'detected' times to 'new' times which place them in the time window of their respective covariant peptides. In the illustrated example, the data point of protein A is shifted backwards. This shift places the data point within time window t, which then is plotted in the adjusted mass spectrum scan shown in FIG. 6C.

There are currently two main techniques that are suitable for ionizing protein molecules for use in mass spectrometry. The first technique is electrospray (ESI) (or similarly, nanospray (nanoESI)) which is applied to liquid phase analytes. ESI has the advantage that it allows direct, online throughput of analytes through the channels of a column or microfluidic device to the electrospray tip where ionization takes place. In the context of the present invention, proteins can thus flow directly and sequentially with high-throughput through the separation phase and the digestion phase up to an ionization phase at the ion source of a mass spectrometer. One of the benefits of ESI is that analytes are usually multiply charged during ionization rather than singly charged. The fragmentation of doubly charged ions produces spectra richer in information for amino acid sequence determination and database searching. ESI is a flowing technique which limits the amount of time available to perform MS/MS analysis of ions. ESI is best suited to online high-throughput MS/MS in which peptides are fragmented and sequence information is derived there from.

In matrix-assisted laser desorption ionization (MALDI), the products of the digestion phase are prepared as separate samples by mixing them in solution with a solid matrix material and depositing the mixture in individual spots on a MALDI support plate. Each spot on the support plate thus contains covariant peptides in crystallized form when the deposition is timed in accordance with the elution time windows of the covariant peptides. The MALDI process is performed offline, i.e., it is not a flow-through process. The mixing of matrix with the sample is critical to the ionization process. On the other hand, an advantage of MALDI is that since it is off-line, more time is available to interrogate the sample. This makes it ideal for protein characterization since the sample can be thoroughly analyzed.

Either ionization technique can be used in the context of the present invention depending on which advantages are sought in a given investigation. For downstream analysis, it is useful to employ a mass spectrometer that produces accurate mass results over a wide spectrum, such as a Time-of-Flight (TOF), Fourier Transform Ion Cyclotron Resonance (FT-ICR), Orbitrap or Magnetic Sector spectrometer. A TOF is particularly useful in tandem MS/MS systems.

Having described the present invention with regard to specific embodiments, it is to be understood that the description is not meant to be limiting since further modifications and variations may be apparent or may suggest themselves to those skilled in the art. It is intended that the present invention cover all such modifications and variations as fall within the scope of the appended claims.

What is claimed is:

1. A method of analyzing a sample comprising multiple protein species, comprising:
   separating the proteins by species such that the multiple protein species emerge in a sequential order;
   subjecting to digestion all species of the separated proteins in the sequential order in which they emerge from the separating; and
   introducing the digested proteins into a mass spectrometer in the sequential order; wherein, within a time window, the digested proteins introduced into the mass spectrometer are covariant.

2. The method of claim 1, further comprising: prior to separating, pre-fractionating the sample comprising the multiple protein species.

3. The method of claim 1, wherein the digestion is performed incompletely such that a portion of the separated proteins are not digested and are introduced in their original form with their corresponding covariant digested proteins into the mass spectrometer.

4. The method of claim 1, wherein the digestion is performed incompletely such that none of the original protein is undigested and introduced intact into the mass spectrometer.

5. The method of claim 1, wherein the digestion is performed completely while substantially all of the separated proteins are broken down into peptides.

6. The method of claim 1, further comprising:
   introducing undigested protein into the mass spectrometer within the same time window that the covariant digested proteins corresponding to the protein are introduced into the mass spectrometer.

7. The method of claim 6, wherein the introducing is performed by combining the undigested protein with an effluent of covariant digested proteins after the digested proteins emerge from the digestion.

8. The method of claim 6, wherein the introducing is performed by delivering the undigested protein and the covariant digested proteins to separate inlet ports of an ionization source of the mass spectrometer.

9. The method of claim 1, further comprising:
   ionizing the digested proteins using electrospray ionization (ESI).

10. The method of claim 9, further comprising:
    MS/MS analysis of the digested proteins by mass selection of a peptide ion followed by one of collision induced dissociation or electron-capture dissociation and another stage of mass analysis.

11. The method of claim 1, further comprising:
    introducing undigested protein into the mass spectrometer;
    mass analyzing the undigested protein; and
    matching the undigested protein with peptides covariant with the undigested protein after mass analysis.

12. The method of claim 11, wherein the matching comprises:
    determining a time difference between the introducing of the undigested protein into the mass spectrometer and the introducing of the digested peptides covariant with the undigested protein; and
    time-shifting data corresponding to the undigested protein by the determined time difference.

13. The method of claim 11, wherein the separating, digestion and introducing occur sequentially in a first flow path.

14. The method of claim 13 further comprising:
    after the separating, diverting a portion of the separated proteins along a second flow path, the diverted portion not being digested; and
    recombining the undigested separated proteins into the first flow path.

15. The method of claim 1, wherein the separating and digestion are performed within a microfluidic device.

16. The method of claim 15, wherein the microfluidic device is coupled to an inlet of the mass spectrometer.

17. The method of claim 1, wherein the separating is performed using reverse phase chromatography.

18. The method of claim 1, wherein the digestion is performed by enzymes.

19. The method of claim 18, further comprising:
    varying a concentration of the enzymes used in the digestion.

20. A method of preparing a sample comprising multiple protein species for use in matrix-assisted laser desorption ionization (MALDI), the method comprising:
    separating the proteins by species such that the multiple protein species emerge in a sequential order;
    subjecting to digestion all species of the separated proteins in the sequential order in which they emerge from the separating;
    depositing each group of covariant digested proteins emerging from the digestion with matrix material onto a spot of a MALDI support plate.

21. The method of claim 20, wherein the digestion is performed incompletely such that a portion of a separated protein is not digested and is combined in its original form with corresponding covariant digested proteins in a spot on the MALDI support plate.

22. The method of claim 20, further comprising:
    combining an undigested protein with an effluent of covariant digested proteins after the digested proteins emerge from the digestion; and
    depositing the undigested protein along with its corresponding covariant digested peptides onto a spot of the MALDI support plate.

23. The method of claim 22, further comprising:
    ionizing undigested protein and covariant digested proteins from a spot on the support plate;
    obtaining a mass spectrum including the undigested protein and the covariant digested proteins; and
    determining a peptide mass fingerprint of the protein from the mass spectrum.

24. The method of claim 23, further comprising:
    MS/MS analysis of the digested proteins by mass selection of a peptide followed by one of collision induced dissociation or electron-capture dissociation and another stage of mass analysis.

* * * * *